(12) United States Patent
Field et al.

(10) Patent No.: US 6,790,186 B1
(45) Date of Patent: Sep. 14, 2004

(54) DEVICE FOR EVALUATING THE DYNAMIC, MECHANICAL PROPERTIES OF MATERIALS

(75) Inventors: John Sugden Field, Berowra Heights (AU); Michael Vincent Swain, Turramurra (AU); Richard Charles Appleyard, Bilgola Plateau (AU)

(73) Assignee: University of Sydney, Sydney (AU)

( * ) Notice: Subject to any disclaimer, the term of this patent is extended or adjusted under 35 U.S.C. 154(b) by 100 days.

(21) Appl. No.: 10/009,766

(22) PCT Filed: Jun. 5, 2000

(86) PCT No.: PCT/AU00/00632
§ 371 (c)(1),
(2), (4) Date: Apr. 11, 2002

(87) PCT Pub. No.: WO00/75624
PCT Pub. Date: Dec. 14, 2000

(30) Foreign Application Priority Data

Jun. 4, 1999 (AU) .............................................. PQ0778

(51) Int. Cl.$^7$ ............................. A61B 5/103; G01N 3/38
(52) U.S. Cl. ............................. 600/587; 73/573; 73/579
(58) Field of Search ................................ 600/300, 398, 600/399, 405, 438, 552, 553, 547, 561, 587, 595; 73/78, 81, 573, 579; 433/72; 702/33, 41–43

(56) References Cited

U.S. PATENT DOCUMENTS

| | | | | |
|---|---|---|---|---|
| 4,132,224 A | | 1/1979 | Randolph | |
| 4,159,640 A | * | 7/1979 | Leveque et al. | ................ 73/81 |
| 5,494,045 A | * | 2/1996 | Kiviranta et al. | ........... 600/587 |
| 5,503,162 A | * | 4/1996 | Athanasiou et al. | ........ 600/587 |
| 5,518,008 A | * | 5/1996 | Cucchiaro et al. | .......... 600/590 |
| 5,701,913 A | | 12/1997 | McPherson et al. | |
| 5,766,137 A | * | 6/1998 | Omata | ........................ 600/587 |
| 5,904,658 A | * | 5/1999 | Niederauer et al. | ......... 600/587 |
| 5,911,694 A | * | 6/1999 | Ikeda et al. | .................. 600/587 |
| 6,068,604 A | * | 5/2000 | Krause et al. | .............. 600/587 |

FOREIGN PATENT DOCUMENTS

EP        0 702 942 A1      3/1996

* cited by examiner

*Primary Examiner*—Charles Marmor
(74) *Attorney, Agent, or Firm*—Greenberg Traurig, LLP; Charles Berman, Esq.

(57) ABSTRACT

A device (10) for evaluating dynamic, mechanical properties of materials includes an elongate cylindrical housing (12) projecting from a handle (14). The housing (12) defines a passage (16). One end of the passage (16) is closed off by a plug (18) with an opposed end of the passage (16) having an end cap (20). A resiliently flexible beam (22) is arranged in a cantilevered manner in the passage (16). A probe (24) is arranged at a free end of the beam (22). A strain gauge array (28) is mounted on the beam (22) for monitoring the deflection of the beam (22) and for generating an output signal representative of the movement of the beam (22). A method for evaluating dynamic, mechanical properties of materials is also disclosed.

15 Claims, 6 Drawing Sheets

DEVICE FOR EVALUATING THE DYNAMIC, MECHANICAL PROPERTIES OF MATERIALS

FIELD OF THE INVENTION

This invention relates to the evaluation of the dynaminc, mechanical properties of materials. More particularly, the invention relates to a device for, and a method of, evaluating the dynamic, mechanical properties of materials. The invention has particular, but not necessarily exclusive, application in the measurement of the dynamic, mechanical properties of materials in the medical field such as, for example, articular cartilage, other tissue, synovial fluid, or the like.

BACKGROUND TO THE INVENTION

Articular cartilage is a connective tissue, which covers the ends of bones in synovial joints of humans and animals. It is relatively soft—about 1000 times less stiff than bone with a smooth whitish appearance in young joints and a rough yellowish appearance in old joints. Articular cartilage has a number of functions which include, 1) minimising contact stress by distributing joint loading, 2) dissipating some of the energy associated with load bearing and 3) permitting near frictionless motion between articulating surfaces.

Diseases (such as arthritis) often lead to joint inflammation and damage to articular cartilage resulting in the need for surgical intervention. Alleviation of pain and disability may involve medical treatment or surgical excision of damaged or degenerate cartilage. In the operating theatre the choice of procedure is often based on arthroscopic examination of the cartilage surfaces. This method is sometimes insecure and does not give any indication of sub-surface degradation. Early diagnosis of osteoarthritis is essential to avoid progression to the clinical stage as once erosion has occurred the disease is irreversible. In nearly all cases of symptomatic patients presenting with visually normal cartilage, the cartilage is found to be softened when probed. Indeed softening of cartilage is one of the earliest observable changes caused by osteoarthritis.

A significant amount of research has been carried out in vitro on the mechanical properties of cartilage using bench top materials testing apparatus. A number of measuring instruments for assessing the mechanical properties of cartilage in-vivo have been proposed (see, for example U.S. Pat. No. 4,364,399, U.S. Pat. No. 5,494,045, U.S. Pat. No. 4,132,224, U.S. Pat. No. 5,503,162). In general, each of these devices measures the surface stiffness of cartilage by means of a probe, which depresses the cartilage locally and from the force resisting penetration determines the local static stiffness. While this method has been found to provide more information about sub-surface degradation it does not fully characterise the properties of the cartilage, which must respond to dynamic loading. This invention provides for dynamic evaluation of the cartilage by causing the probe to depress the surface of the cartilage in an oscillatory manner.

SUMMARY OF THE INVENTION

According to a first aspect of the invention, there is provided a device for evaluating dynamic, mechanical properties of materials, the device including
  a housing;
  a resiliently flexible beam displaceably arranged relative to the housing so as to be displaceable in a reciprocatory manner relative to the housing upon the application of an electric field, the beam comprising a bimorph being a laminate of at least two piezoelectric materials;
  an engaging means carried by the beam for engaging the material to be evaluated; and
  a deflection measuring means arranged on the beam for measuring displacement of the beam.

Preferably, the piezoelectric materials are piezoelectric ceramic materials.

The manner in which the beam is attached to the housing will depend on the application of the device. In one embodiment of the invention, the beam may be arranged in a cantilevered fashion to extend from a support in the housing with the engaging means, which may be in the form of a probe, arranged at a free end of the beam.

The engaging means may extend from the beam. Once again, depending on the application of the device, the engaging means may extend at an angle to the beam or may be in line with the beam. In the latter case, the engaging means may project from an end of the beam.

In another embodiment of the invention, the beam may be supported at both ends to be able to flex in its central region under the application of the electric field. The engaging means may then be arranged in the central region of the beam.

The electric field applied to the beam may be in the form of a voltage arising from a voltage generating means which generates an AC signal of the appropriate frequency or frequencies.

The deflection measuring means may be in the form of a strain gauge array attached to the beam. Where the beam is mounted in a cantilevered fashion, the array may be arranged at, or adjacent, the mounted end of the beam. In the case where the beam is supported at both ends, the array may be arranged at, or adjacent, one or both ends of the beam.

In the case where the device has the beam mounted in a cantilevered fashion, the device may include a plug received in the housing. One end of the plug may serve as an anchor for the beam. An opposed end of the plug may have an electrical connecting means for connection to a complementary electrical connector.

In the case where the beam is supported at both ends, the housing may include support members extending from a floor of the housing on which the beam rests.

The device may include a processing means connectable to the deflection measuring means for assessing the dynamic behaviour of the beam, in use, to evaluate the dynamic, mechanical properties of the material.

In one embodiment, the processing means may be operable to determine a first signal with the engaging means out of contact with the material and at least one further signal with the engaging means in contact with the material and a combining means for combining the signals so as to separate the influence of the beam and the engaging means from the material being evaluated.

In use, the voltage generating means which generates the oscillating electric field may generate a complex waveform signal to enable the dynamic properties of the material to be determined over a range of frequencies.

In another embodiment, the processing means may incorporate an electronic unit for monitoring a force resisting penetration or displacement of the material by the engaging means and the motion of the engaging means. This electronic unit may include a load-sensing element in the form of a piezoelectric load cell and associated electronic circuitry. The associated electronic circuitry may incorporate a field effect transistor.

The electronic unit may be interposed between the engaging means and the beam and may be sealed in a fluid-impervious casing.

According to a second aspect of the invention, there is provided a method of evaluating dynamic, mechanical properties of materials, the method including the steps of     urging an engaging means into contact with a material to be evaluated, the engaging means being carried on a resiliently flexible beam responsive to an electric field, the beam being a bimorph comprising a laminate of at least two piezoelectric materials;

applying an oscillating electric field to the beam to cause it to oscillate at a predetermined frequency so that the engaging means periodically applies a deforming force to the material;

monitoring the dynamic behaviour of the beam as it oscillates; and     extracting from the monitored, dynamic behaviour of the beam, data relating to the dynamic, mechanical properties of the material.

The method may include exciting the beam with a complex waveform signal.

The method may include using data generated by the oscillation of the beam under the influence of said signal to determine the dynamic, mechanical properties of the material at different frequencies.

The method may include obtaining a first signal with the engaging means out of contact with the material and at least one further signal with the engaging means in contact with the material and combining the signals so as to separate the influence of the engaging means from the material being evaluated.

Thus, the method may include using the signals to form transfer functions. Finally, the method may include processing the transfer functions to simultaneously give values of the dynamic properties of the material at a range of frequencies.

BRIEF DESCRIPTION OF THE DRAWINGS

The invention will now be described by way of example with reference to the accompanying drawings, in which.

DETAILED DESCRIPTION OF THE DRAWINGS

Figure 1:
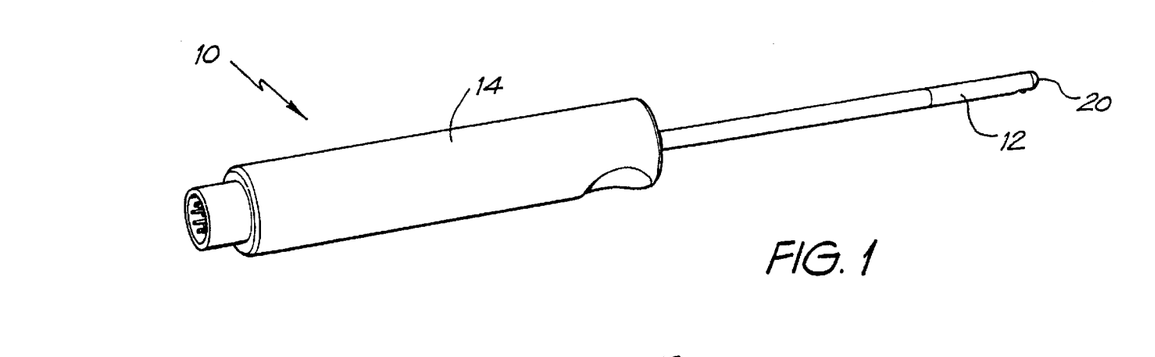
FIG. 1 shows a three dimensional, schematic view of a device, in accordance with a first embodiment of the invention, for evaluating dynamic, mechanical properties of materials.
Figures 2, 3:
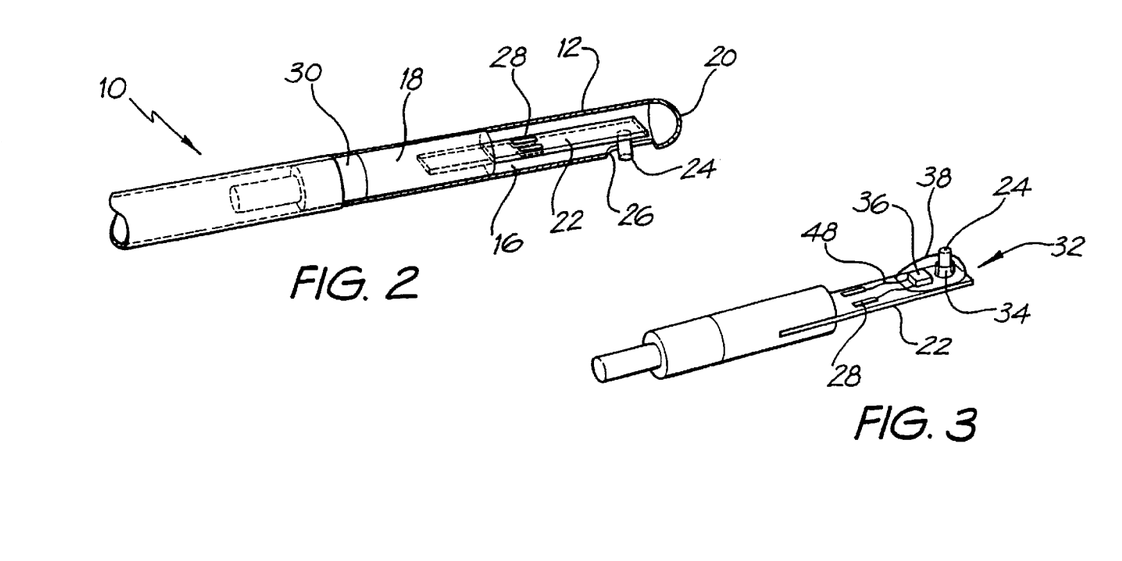
FIG. 2 shows a three dimensional, sectional, schematic view of one embodiment of the device.
FIG. 3 shows a three dimensional, schematic view of part of another embodiment of the device.

In FIGS. 1 to 3 of the drawings, reference numeral 10 generally designates a device, in accordance with a first embodiment of the invention, for evaluating dynamic, mechanical properties of materials. The device 10 of this embodiment is intended particularly for use in the evaluation of articular cartilage and will be described with reference to that application. The device 10 includes an elongate cylindrical housing 12 projecting from a handle 14 which facilitates manipulation of the housing 12 by an operator such as a surgeon. The housing 12 defines a passage 16 (FIG. 2). One end of the passage 16 is closed off by a plug 18. An opposed end of the passage 16 has an end cap 20.

A resiliently flexible beam 22 is arranged cantilever-fashion in the passage 16. The beam 22 extends from one end of the plug 18. The beam 22 is in the form of a piezoelectric bimorph.

An engaging means, in the form of a probe 24, is arranged at a free end of the beam 22. The probe 24 extends at substantially right angles to a longitudinal axis of the beam 22 and protrudes through an opening 26 defined by registering recesses at an end of the housing 12 and the end cap 20. Although not shown, the opening 26 is closed by a resiliently flexible gasket for inhibiting the ingress of detritus into the interior of the housing 12.

A deflection measuring means in the form of a strain gauge array 28 is mounted on the beam 22 adjacent its cantilevered mounting to the plug 18.

An end of the plug 18, opposite the end from which the beam 22 projects, incorporates electrical connections, for example, female connections which are engaged by complementary electrical connectors on a connector element 30 for connection to a processing means such as a computer (not shown).

It is to be noted that the end cap 20 and that end of the housing 12 supporting the end cap 20 may have a diameter greater than that of the remainder of the housing 12 to form a bulbous end to facilitate access to the in-situ and in-vivo articular cartridge. The enlarged, rounded surface also provides a reference surface which, when brought into contact with the cartilage, causes the probe 24 to apply a small force perpendicular to the surface with which the probe 24 is in contact.

In the embodiment of the invention illustrated in FIG. 2 of the drawings, the stiffness of the cartilage is deduced from the changes in dynamic behaviour of the beam 22 when the probe 24 is in contact with the cartilage relative to the behaviour of the beam 22 when the probe 24 is not in contact with the cartilage.

Thus, in use, an oscillating electric field is applied to the beam 22. Due to the piezoelectric bimorph construction of the beam 22, the application of the electric field causes the beam 22 to oscillate in a predetermined manner. This, in turn, causes the probe 24 to apply and remove a force to the cartilage in the same manner.

The dynamic behaviour or the mechanical response of the beam 22, with the probe 24 in contact with the cartilage, is determined in terms of Fourier transforms. It can be shown that, for a linear response, usually a transfer function representing the system comprising the beam 22 with its probe 24 in contact with the cartilage is the product of two Fourier transforms. One Fourier transform represents the beam 22 with its probe 24 not in contact with the cartilage and a second Fourier transform represents the behaviour of the cartilage. Both of these Fourier transforms are complex quantities having a real (in-phase) component and an imaginary (90° out of phase) component. These components are used to obtain the local stiffness of the cartilage and a loss tangent which, in conjunction, give an indicative measure of the extent of degradation, if any, of the cartilage.

The Fourier transforms are formed from the instantaneous voltages applied to the bimorph beam 22 and instantaneous voltages returned by the strain gauge array 28. These Fourier transforms are, preferably, calculated using a composite or complex waveform.

As indicated above, the Fourier transforms representing the cartilage may be separated into real and imaginary components.

The force, F(w), exerted on the probe 24 by the material, may be determined from the relationship between the force necessary to reduce the free deflection of the beam 22 and the force measured when the probe 24 is in contact, for a given voltage applied to it, and using the known mechanical Characteristics of the beam 22. The displacement, H(w), of the probe 24 is determined from a relationship of beam deflection when the probe 24 is not in contact with the material and beam deflection when the probe 24 is in contact with the material.

The stiffness and loss tangent of the material may be determined from the transfer function $$K(w) = \frac{F(w)}{H(w)}$$

Hence, in use, signals from the strain gauge array 28 are fed via the plug 18 and the connector element 30 to a processing means (not shown) where the signals 8 are processed to evaluate the dynamic mechanical properties of the articular cartilage.

Referring now to FIG. 3 of the drawings, a second embodiment of the invention is illustrated. With reference to FIGS. 1 and 2, like reference numerals referred to like parts, unless otherwise specified.

In this embodiment of the invention, the processing means of the device 10 includes an electronic unit 32. The electronic unit 32 monitors a force resisting penetration of the material by the probe 24. The electronic unit 32 includes a load sensing device in the form of a piezoelectric load cell 34 interposed between the probe 24 and the beam 22. The load cell 34 is connected to a field effect transistor (FET) 36. The load cell 34 and the FET 36 are encased in a polymeric, fluid-impervious casing 38. Electric leads 48 connect the electronic unit 32 to the plug 18.

In this embodiment of the invention, the dynamic behaviour of the articular cartilage is evaluated as a direct function of the force applied by the probe 24 to the cartilage.

In both embodiments of the invention, local dynamic complex stiffness may be measured over a frequency range for providing even greater information. If measurements at several discrete frequencies extend the intervention excessively, unwanted medical consequences could arise. With the present invention however, measurements of a range of frequencies may be compressed into a period little more than the time required for measurement for a single frequency by the use of a composite waveform. Extraction of complex dynamic stiffness is then achieved using Fourier decomposition methods.

Figure 4:
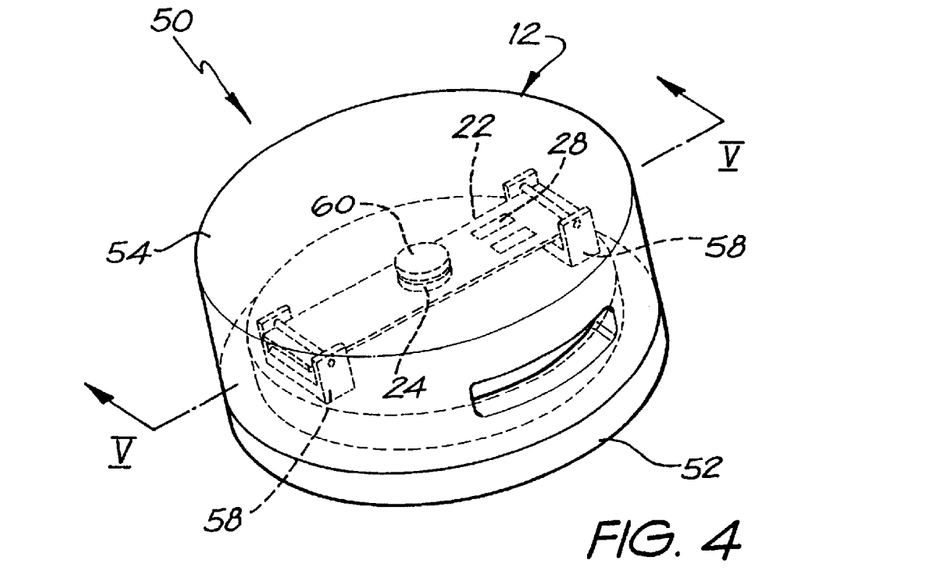
FIG. 4 shows a three dimensional, schematic view of a device, in accordance with a further embodiment of the invention, for evaluating dynamic, mechanical properties of materials.
Figure 5:
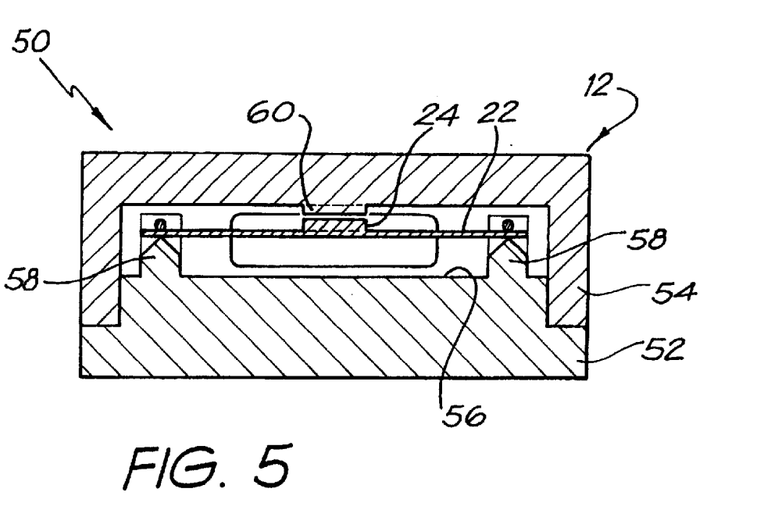
FIG. 5 shows a sectional side view of the device of FIG. 4 taken along line V—V in FIG. 4.

Referring to FIGS. 4 and 5 of the drawings, a device, in accordance with a further embodiment of the invention, is illustrated and is designated generally by the reference numeral 50. With reference to FIGS. 1 to 3 of the drawings, like reference numerals refer to like parts, unless otherwise specified.

In this embodiment of the invention, the housing 12 comprises a base 52 closed off by a removable lid 54. The base 52 defines a floor 56 from which a pair of spaced posts 58 project. The beam 22 is supported on the posts 58 in spaced relationship relative to the floor 56. The beam is constrained against movement at its ends.

This device 50 is intended for use in detecting variations in the visco-elastic properties of body fluids such as synovial fluids. This provides a method to appraise the mechanical health of a joint critically.

Those skilled in the art will appreciate that, in the case of joints where arthritis is present in a joint, it leads to a marked reduction in the magnitude of the visco-elastic properties of synovial fluid in comparison with properties of synovial fluid from a healthy joint.

In this embodiment of the invention, the probe 24 is in the form of a raised disk arranged centrally on the beam 22. The probe 24 is in register with a disk 60 suspended from the lid 54. A quantity of synovial fluid to be tested is placed between the probe 24 and the plate 60. The beam 22 produces deflections and forces at its centre under the control of the electric field arising from the voltage excitation signal.

The "squeezing" motion imparted to the fluid by the probe 24 relative to the upper plate 60 is monitored.

As in the case of the previous embodiment, the bimorph beam 22 is oscillated by means of a complex waveform. Similar means of analysing the signal output from the strain gauge array 28 in response to the load applied to the fluid under investigation are used to determine the characteristics and properties of the fluid. More particularly, the analysis produces a transfer function which is related to the visco-elastic properties of the fluid under, investigation by using mathematical models as described above.

Figure 6:
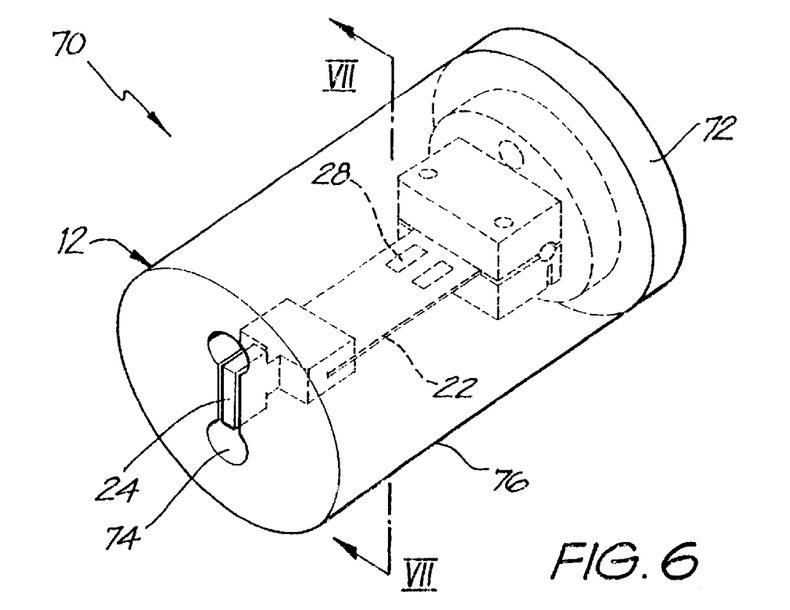
FIG. 6 shows a three dimensional, schematic view of a device, in accordance with yet a further embodiment of the invention, for evaluating dynamic, mechanical properties of materials.
Figure 7:
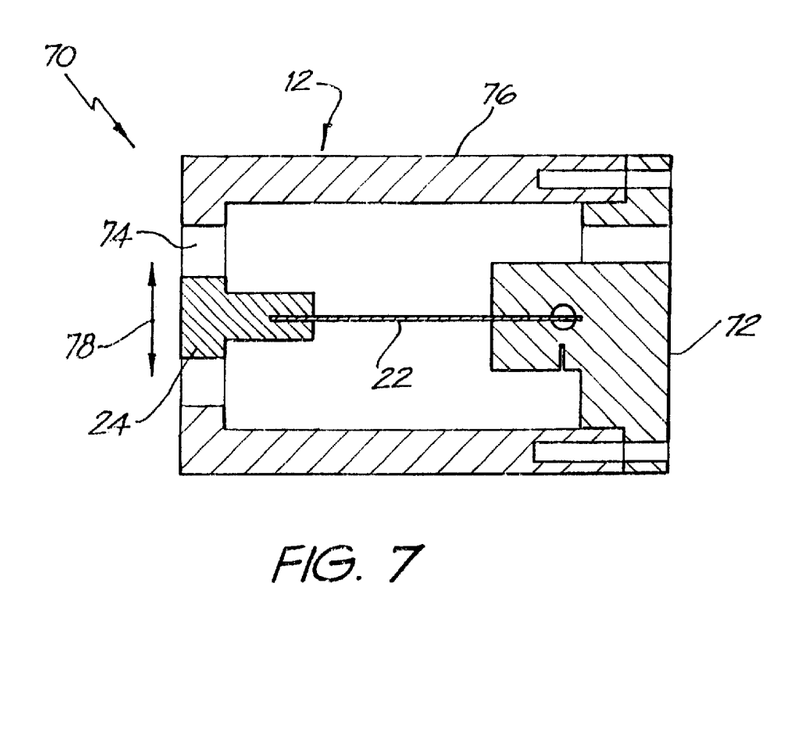
FIG. 7 shows a schematic, sectional side view of the device of FIG. 6 taken along line VII—VII in FIG. 6.

Referring, now to FIGS. 6 and 7 of the drawings, yet a further embodiment of the invention is illustrated and is designated generally by the reference numeral 70. Once again, with reference to the previous drawings, like reference numerals refer to like parts, unless otherwise specified.

In this embodiment of the invention, the housing 12 includes a support member 72 to which a cylindrical casing 76 is attached. The beam 22 extends in a cantilever-fashion from the member 72. The probe 24 mounted at a free end of the beam 22 and in line with the beam 22 projects through a dumbbell shaped opening 74 in the cylindrical casing 76 of the housing 70.

The probe 24 is received in the opening 74 such that an end of the probe 24 lies substantially flush with an end of the casing 76.

The strain gauge array 28 is carried on the beam 22 close to the cantilevered mounting of the beam 22 to the member 72.

The device 70, in accordance with this embodiment of the invention, is intended for measuring the visco-elastic properties of tissue either in vitro or in vivo. Once again, the bimorph beam 22 is subjected to an electric field excitation signal having a complex waveform. The probe 24 is caused to oscillate in the direction of arrows 78 (FIG. 7) in order to place the tissue being evaluated in shear. The signal generated by the strain gauge array 28 is, once again, subjected to a similar analysis as in the previous embodiment producing a transfer function related to the physical properties of the tissue under investigation with the assistance of the mathematical model described previously.

Figure 8:
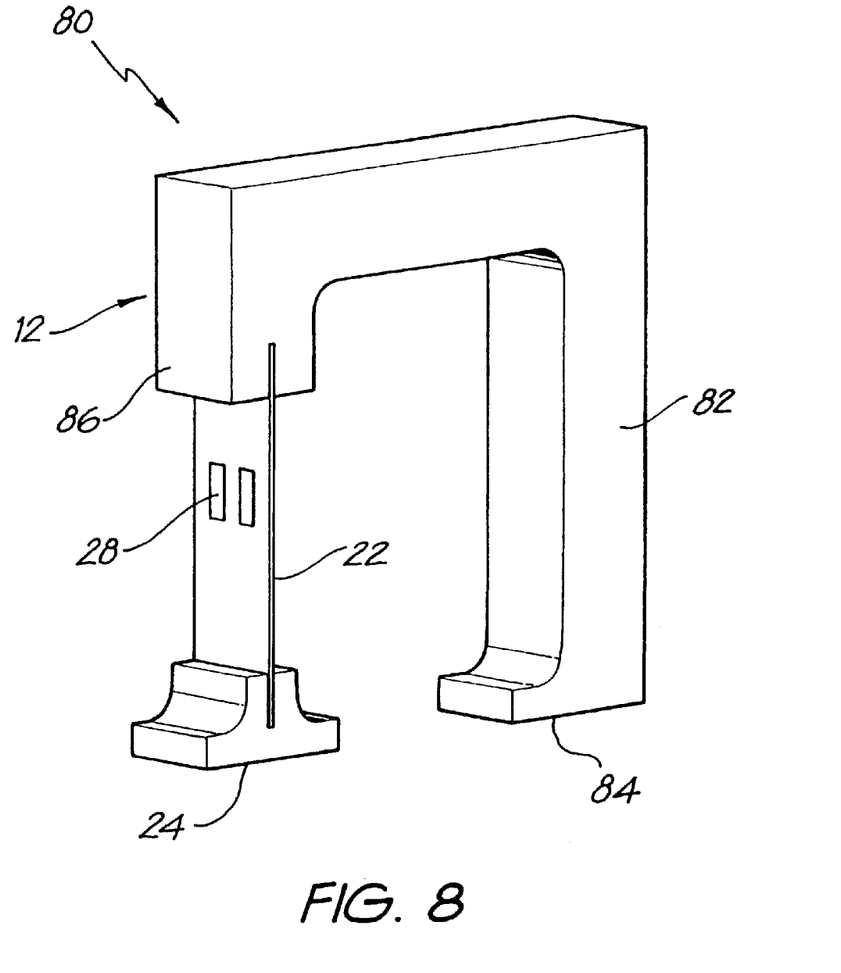
FIG. 8 shows a three dimensional, schematic view of a device, in accordance with still a further embodiment of the invention, for evaluating dynamic, mechanical properties of materials.
Figure 9:
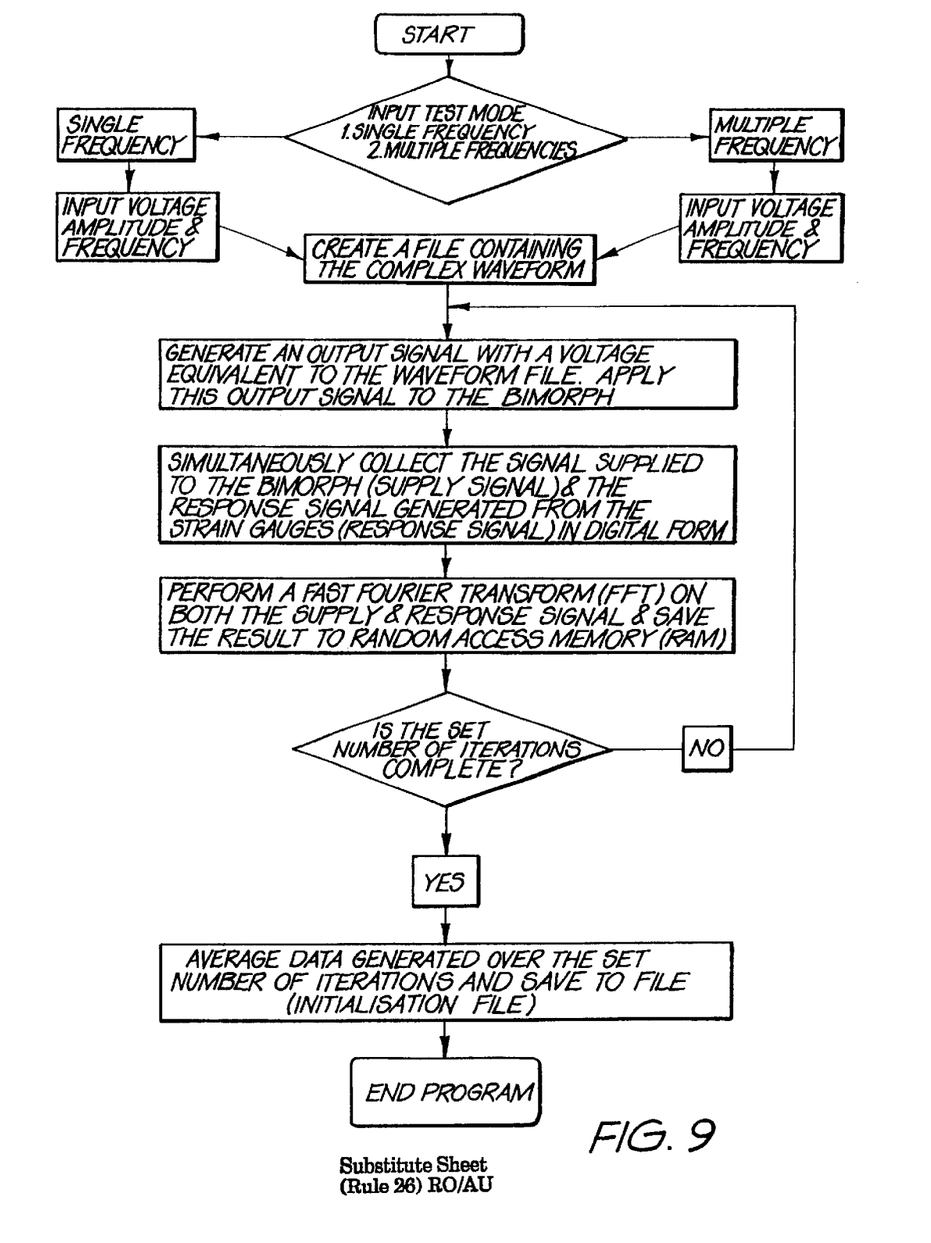
FIG. 9 shows a flow chart of an initialisation procedure for a processing means used with the device.
Figure 10:
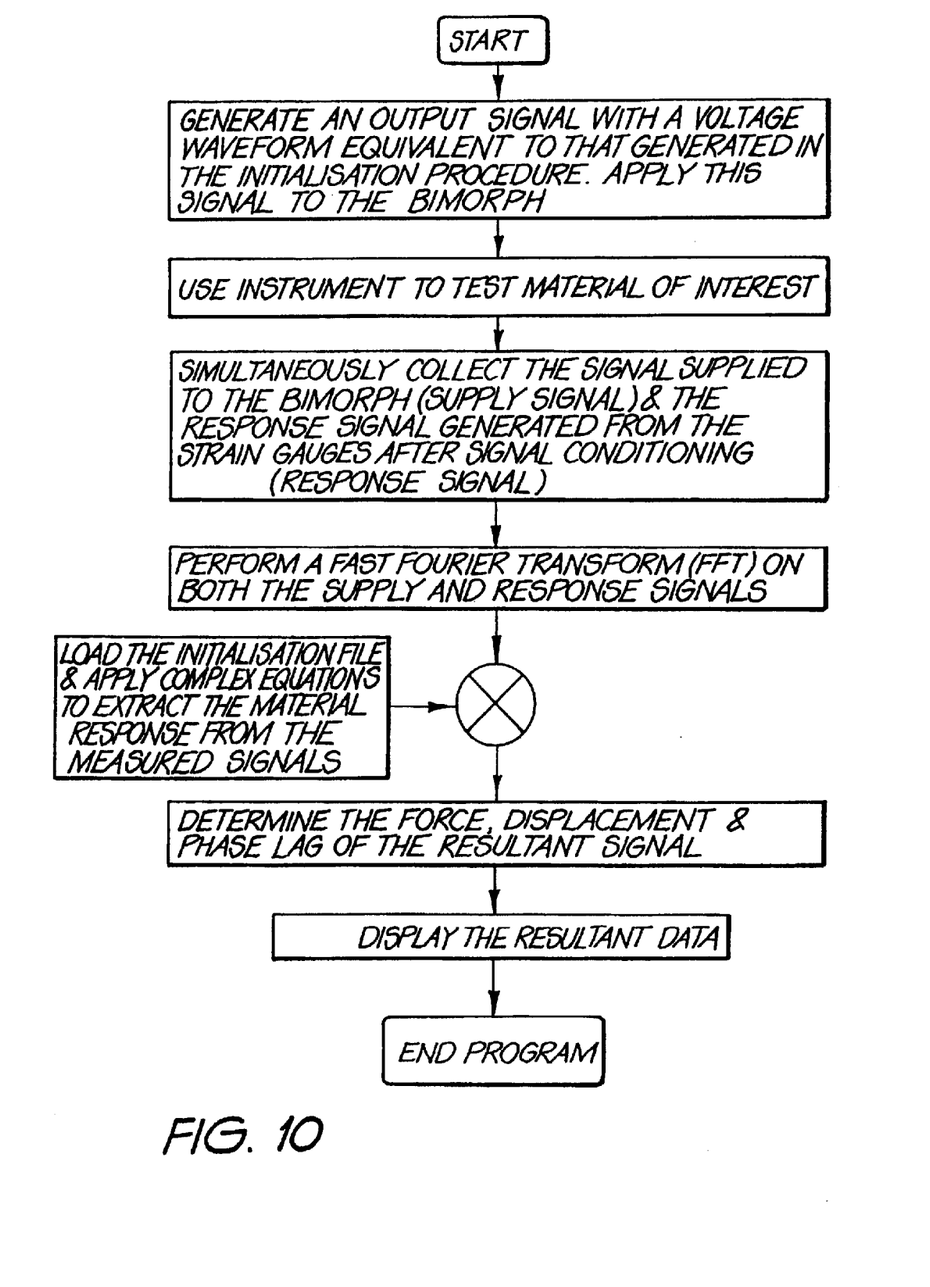
FIG. 10 shows a flow chart of a test procedure for the processing means.

In the embodiment of the invention illustrated in FIG. 8 of the drawings, yet a further device, in accordance with the invention, for evaluating dynamic, mechanical properties of materials is illustrated and is designated generally by the reference numeral 80. Once again, this device 80 is intended for use in detecting variations in the visco-elastic properties of tissue.

In this embodiment, the housing 12 is substantially L-shaped having a limb 82 defining a fixed foot 84. The beam 22 is suspended from a formation 86 of the housing 12 to extend substantially parallel to the limb 82 of the housing 12. The probe 24, in the form of a foot, is arranged on a free end of the beam 22.

The beam 22 is subjected to an excitation signal. The excitation signal has a complex waveform. The feet 84 and 24 of the housing 12 are placed against the tissue and the displacement of the probe or foot 24 relative to the fixed foot 84 loads the tissue in a tension mode.

The detected motion of the beam 22 under the effect of the electric field is monitored by the strain gauge array 28. An output signal from the strain gauge array 28 is analysed to produce a transfer function related to properties of the tissue under investigation with the assistance of the mathematical model.

Yet a further embodiment of the invention which is not illustrated is its potential for use in key-hole surgery. A complaint of surgeons conducting key-hole surgery is the lack of "feel" when remotely operated instruments are used by the surgeon. A crucial element that is missing in much of the surgery is the absence of feel whereby the surgeon is able to sense the scalpel or other instruments passing from one tissue type to another such as, for example, from diseased to normal tissue or vice versa.

It is envisaged that, with the device of the invention in an appropriate configuration a means is provided whereby the scalpel or other device at the end of a manipulator has superimposed on it a small oscillatory motion at fixed, multiple or random frequencies. The strain gauge array determines the forces generated and the relevant phase angle. In other words, in effect, by measuring the dynamic, mechanical properties of the tissue and producing an appropriate signal, a simulation of "feel" can be imparted to the instruments being controlled by the surgeon.

It is a particular advantage of the invention that, due to the oscillatory compression and release of the cartilage, other tissue or fluid by the probe 24, dynamic evaluation of the material can be effected resulting in earlier and more accurate diagnosis. In particular, the dynamic evaluation of the material enables a more accurate evaluation of the material to be made.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A device for evaluating dynamic, mechanical properties of materials, the device including
   a housing;
   a resiliently flexible beam having a pair of opposed ends, the beam being supported only at at least one of the ends of the beam to be suspended relative to the housing and being adapted to be displaced in a reciprocatory manner relative to the housing upon the application of an electric field, the beam comprising a bimorph being a laminate of at least two piezoelectric materials;
   an engaging means carried by the beam for engaging the material to be evaluated; and
   a deflection measuring means arranged on the beam for measuring displacement of the beam.

2. The device as claimed in claim 1, wherein each piezoelectric material is a piezoelectric ceramic material.

3. The device as claimed in any one of the preceding claims, wherein the engaging means extends from the beam.

4. The device as claimed in claim 1, wherein the deflection measuring means is in the form of a strain gauge array arranged on the beam.

5. The device as claimed in claim 1 further including a processing means connectable to the deflection measuring means for assessing the dynamic behaviour of the beam, in use, to evaluate the dynamic, mechanical properties of the material.

6. The device as claimed in claim 5, wherein the processing means is adapted to determine a first signal with the engaging means out of contact with the material and at least one further signal with the engaging means in contact with the material and a combining means for combining the signals to separate the influence of the engaging means from the material being evaluated.

7. The device as claimed in claim 6, further including a voltage generating means for generating an oscillating electric field.

8. The device as claimed in claim 7, wherein the voltage generating means generates a complex waveform signal to enable the dynamic properties of the material to be determined over a range of frequencies.

9. A device as claimed in claim 1 when used in evaluating the dynamic, mechanical properties of any one of the following materials:—articular cartilage; synovial fluid; body tissue.

10. A method of evaluating dynamic, mechanical properties of materials, the method including
    urging an engaging means into contact with a material to be evaluated, the engaging means being carried on a resiliently flexible beam responsive to an electric field, the beam being a bimorph comprising a laminate of at least two piezoelectric materials, the beam being arranged in a housing and the beam having a pair of opposed ends with the beam being supported only at at least one of the ends of the beam to be suspended relative to the housing and being adapted to be displaced in a reciprocatory manner relative to the housing;
    applying an oscillating electric field to the beam to cause the beam to oscillate in a predetermined manner so that the engaging means periodically applies a deforming force to the material;
    monitoring the dynamic behaviour of the beam as the beam oscillates; and
    extracting from the monitored, dynamic behaviour of the beam, data relating to the dynamic, mechanical properties of the material.

11. The method as claimed in claim 10, further including exciting the beam with a complex waveform signal.

12. The method as claimed in claim 11, further including using data generated by the oscillation of the beam under the influence of said signal to determine the dynamic, mechanical properties of the material.

13. The method as claimed in claim 12, further including obtaining a first signal with the engaging means out of contact with the material and at least one further signal with the engaging means in contact with the material and combining the signals so as to separate the influence of the engaging means from the material being evaluated.

14. The method as claimed in claim 13, further including using the signals to form transfer functions.

15. The method as claimed in claim 14 which includes processing the transfer functions to simultaneously give values of the dynamic properties of the material at a range of frequencies.

* * * * *